United States Patent [19]

Haber et al.

[11] Patent Number: 4,773,393
[45] Date of Patent: Sep. 27, 1988

[54] HYPODERMICALLY IMPLANTABLE GENITOURINARY PROSTHESIS

[75] Inventors: Terry M. Haber, Lake Forest, Calif.; Anthony A. Malizia, Jr., Stockbridge, Ga.

[73] Assignee: C. R. Bard, Inc., Murray Hill, N.J.

[21] Appl. No.: 881,830

[22] Filed: Jul. 3, 1986

[51] Int. Cl.[4] .............................................. A61M 5/00
[52] U.S. Cl. ..................................... 600/30; 128/344; 128/DIG. 25; 128/325; 604/274
[58] Field of Search ............... 128/1 R, DIG. 25, 325, 128/343, 344, 1.3, 129; 604/57, 59, 60, 49, 51, 96, 274; 623/6

[56] References Cited

U.S. PATENT DOCUMENTS

| | | | |
|---|---|---|---|
| 3,512,528 | 5/1970 | Whitehead et al. | 128/129 |
| 3,834,394 | 9/1974 | Hunter et al. | 604/99 |
| 4,240,433 | 12/1980 | Bordow | 604/96 |
| 4,373,218 | 2/1983 | Schachar | 623/6 |
| 4,545,367 | 10/1985 | Tucci | 604/96 |
| 4,585,457 | 4/1986 | Kalb | 623/6 |

OTHER PUBLICATIONS

"Polytef(Teflon) Migration after Periurethal Injection: Tracer and X-Ray Microanalysis Techniques in Experimental Study", by A. A. Malizia, Jr. et al., vol. XXX, Trans. Am. Soc. Artif. Intern. Organs, 1983, pp. 330-334.
"Migration and Granulomatous Reaction after Periuretral Injection of Polytef(Teflon)", by Anthony A. Malizia, Jr. et al., vol. 251, Journal of the A.M.A., Jun. 22/29, 1984, pp. 3277-3281.
"Periurethral Polyetrafluoroethylene Injections in Incontinent Female Subjects with Neurogenic Bladder Disease", by Robert I. Lewis et al., vol. 131, Journal of Urology, Mar. 1984, pp. 459-462.
"Periurethral Polytrafluorethylene Injection for Urinary Incontinence", by Victor A. Politano, vol. 127, Journal of Urology, Mar. 1982, pp. 439-442.
"Endoscopic Injections of Teflon to Treat Urinary Incontinence in Women", British Medical Journal, vol. 288, 21 Jan. 1984, p. 192.

Primary Examiner—Dalton L. Truluck
Assistant Examiner—Frank Wilkens
Attorney, Agent, or Firm—Morland C. Fischer

[57] ABSTRACT

Apparatus for hypodermically implanting a genitourinary prosthesis comprising an extensible, inflatable tissue expanding containment membrane to be located in the proximal periurethral tissues to add bulk to these tissues and thereby overcome urinary incontinence by means of localized, controlled tissue volume increase. Hypodermic positioning, injecting and inflating instruments are also disclosed for implanting the containment membrane and for percutaneously infusing the membrane with biocompatible fluid or suspended particulate matter. The containment membrane functions as an envelope for retaining the fluid or particulate matter therewith in while controllably and advantageously increasing localized tissue volume and simultaneously preventing the migration of such fluid or particles. Accordingly, an increased passive occlusive pressure may be applied to the patient's urethra to achieve continence.

7 Claims, 1 Drawing Sheet

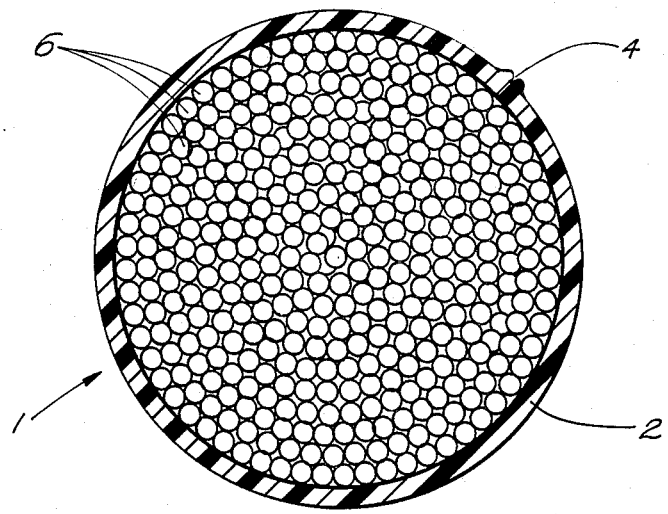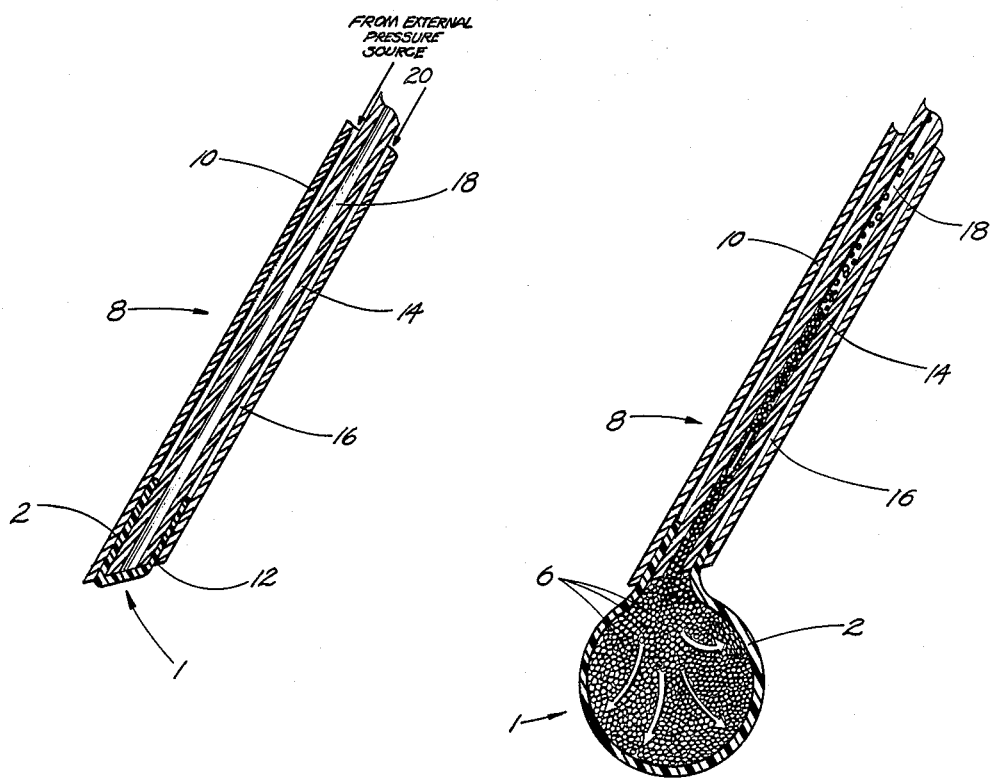

HYPODERMICALLY IMPLANTABLE GENITOURINARY PROSTHESIS

BACKGROUND OF THE INVENTION

1. Field of the Invention

This invention relates to an inflatable genitourinary prosthesis and to hypdermic injecting instruments for positioning, injecting and inflating the prosthesis so that increased occlusive pressure may be accurately applied to a patient's urethra for holding the patient continent. The prosthesis includes an expandable anti-migration membrane which may be percutaneously infused with fluid or suspended particulate matter so as to increase localized tissue volume while preventing the possible migration of such fluid or particulate matter.

2. Prior Art

As will be known to those skilled in the art, in cases where the natural sphincter muscles of a patient have been surgically excised, damaged by disease or compromised by physical trauma, an artificial prosthetic sphrincter has often been implanted so that occlusive pressure may be applied to the urethra to restore continence. Artificial sphincters are well-known and specific examples thereof will not be listed. However, the implantation of an artificial sphincter commonly requires a major surgical procedure which necessitates the hospitalization of the patient. Such a procedure is relatively complex and expensive, and usually requires six to eight weeks or more of recovery time. In most cases, the patient also faces approximately two months delay before activation of the prosthesis to even ascertain whether the surgery has been successful (i.e. the patient is continent). More particularly, because of the swollen and aggravated condition of edema of the urethral tissues during, and for a period subsequent to surgery, the physician cannot precisely match the occlusive pressure to the patient's urethra. Therefore, the physician must estimate the required minimal occlusive pressure needed to achieve continence in that particular patient. As a consequence of such estimate, sphincteric mechanisms are often improperly selected or fitted, so that the occlusive pressures generated by such mechanisms are either insufficient to successfully achieve continence or excessive to the point of causing ischemia and subsequent erosion of urethral tissue. Excessive circumferential occlusive forces will eventually effect blood flow to the urethra and thereby cause ischemia and subsequent erosion. Also, if the implant surgery should prove to be unsuccessful (i.e. the maximum occlusive pressure to be generated by the sphincter is insufficient to hold the patient continent or the sphincter malfunctions mechanically), then additional surgery becomes necessary to provide sphincter adjustment, repair or explant.

Reference is now made to "Migration And Granulomatous Reaction After Periurethral Injection Of Polytef (Teflon)" by Anthony A. Malizia, Jr. et al, *Journal of the A.M.A.*, June 22/29, 1984, Vol. 251, No. 24, pp. 3277-3281. It has been demonstrated in humans that urinary incontinence may be successfully treated by non-surgical means with periurethral injection of polytef paste to increase localized tissue volume and thereby increase external occlusive pressure to the urethra for causing a partial obstruction and, thus, continence. However, this article reveals wide spread migration of polytef particles from the injection site. In addition, such paste was found to induce tissue reaction with TEFLON granulomas. Because of the possible toxicity of TEFLON-based paste, concern for patient safety has also been expressed. Hence, an otherwise sound, non-surgical procedure has now experienced reduced application.

SUMMARY OF THE INVENTION

Briefly, and in general terms, this invention relates to a unique genitourinary prosthesis for treating urinary incontinence. The prosthesis comprises an extensible and inflatable elliptoidal-or pyriform-shaped membrane to be periurethraly or perineally injected or implanted to form an enclosure for receiving and containing a supply of fluid or suspended particulate matter. In this manner, the membrane is precisely and controllably inflated while in situ so as to add bulk and thereby apply increased localized tissue volume and proportionately greater external occlusive pressure to the urethral mucosa to restore the patient's continence. Adding bulk to the peripurethral tissues increases the external pressure around the proximal urethra which restores continence by causing a partial obstruction. However, the previous problem of particle migration is solved by virtue of the antimigration membrane in which the fluid or particulate matter are retained.

The genitourinary prosthesis of this invention is implanted by means of specialized dual hypodermic positioning, injecting and inflating instrument. The dual hypodermic instrument includes a hollow outer trocar to surround the containment membrane and dilate a suitably sized insertion channel through the targeted patient tissues. Located within the outer trocar is a hollow stylus which communicates with the interior of the containment membrane for placing the membrane in communication with a source of fluid or suspended particulate matter. With the containment membrane percutaneously implanted in the proximal urethra, the membrane is then infused, via the stylus, with a measured supply of fluid or particulate matter, whereby to inflate the membrane. An inflation of the membrane proportionately increases local tissue volume in the periurethral tissues to correspondingly increase the occlusive pressure applied to the proximal urethra tissues for restoring a patient's continence. The positioning, injecting and inflating instrument is then withdrawn from the periurethral tissues leaving the inflated containment membrane in the form of an envelope for preventing the undesirable migration of the fluid or particulate matter while adding the desired tissue bulk to cause a partial obstruction. One or more of the genitourinary prosthesis of the present invention may be implanted, as just described, depending upon etiology, residual sphincteric function, vascularity and physical properties of that individual patient's urethral tissues.

BRIEF DESCRIPTION OF THE DRAWINGS

FIG. 1 shows the genitourinary prosthesis of the present invention in an inflated state and filled with fluid or suspended particulate matter;

FIG. 2 shows the dual hypodermic positioning, injecting and inflating instrument for implanting the prosthesis of FIG. 1; and FIG. 3 shows the dual hypodermic instrument of FIG. 2 with the prosthesis of FIG. 1 being percutaneously infused with a measured supply of fluid or suspended particulate matter.

DESCRIPTION OF THE PREFERRED EMBODIMENT

Referring to FIG. 1 of the drawings, there is shown an expandable and inflatable prosthesis 1 in an expanded and inflated state (i.e. filled with fluid or suspended particulate matter). The prosthesis 1 of this invention will be described in its preferred embodiment as a genitourinary prosthesis for returning a patient to continence by producing a controlled increase in localized tissue volume and a corresponding greater passive occlusive pressure. However, it is to be expressly understood that the prosthesis 1 is not limited to the treatment of urinary continence, but has other applications including, but not limited to, a variable volume mass to replace surgically removed tissue and/or organ excisions or as an injectable anti-urethral reflux mass. Still further applications of the present invention include an injectable testicular prosthesis, injectable prosthetic eye, prosthetic sphincter and injectable intraocular lens. What is more, the prosthesis may be formed from a selectively permeable (by a gas or liquid) material which can be implanted as a controlled release drug delivery system.

According to the preferred embodiment of this invention, the genitourinary prosthesis 1 comprises a generally elliptoidal or pyriform-shaped containment membrane that is preferably formed from a suitable tear-resistant, biocompatible, elastomeric material, such as, for example, polyurethane, silicone, latex, or the like. The containment membrane 2 contains a normally closed orifice 4 through which biomeric fluid or suspended particulate matter 6 is percutaneously injected to inflate membrane 2. By way of example, the material 6 which is injected through orifice 4 may include TEFLON particles or spheres, radio-opaque isotonic fluid, physiologic saline solution, and the like. Hypodermic instruments for positioning, injecting and inflating containment membrane 2 will be disclosed in greater detail hereinafter when referring to FIGS. 2 and 3.

In the inflated condition of FIG. 1, the containment membrane 2 serves as a non-permeable envelope for preventing the migration of the material 6 contained therewithin. Moreover, the containment membrane may be precisely and controllably infused with the minimum volume of fluid or suspended particulate matter necessary for achieving continence while simultaneously minimizing the risk of impeding arteriovascular blood flow through the urethra, as a consequence of ischemia.

A dual hypodermic needle 8 for implanting the prosthesis 1 is now described while referring to FIG. 2 of the drawings. The dual hypodermic needle 8 includes a hollow, cylindrical outer trocar 10. Outer trocar 10 is formed from a structurally sound and corrosion-resistant material, such as titanium, or the like. Trocar 10 functions as an outer casing to protect the integrity of the guide the containment membrane 2 during implantation. Trocar 10 also functions as a cutting instrument by which to dilate a suitably sized channel through the patient's urethral mucosa, so that the prosthesis 1 may be suitably located (e.g. within the bulbar urethra of the corpus spongiousum). In this regard, trocar 10 is provided with a sharp, oblique cutting end 12 for establishing the subcutaneous channel (not shown) through which to insert prosthesis 1.

Located within outer trocar 10 is a hollow, cylindrical inner stylus 14. Stylus 14 is also preferably formed from a suitable material, such as titanium, or the like. Outer trocar 10 and inner stylus 14 are concentrically aligned with and spaced from one another, so that a narrow channel 16 is formed therebetween. Located within channel 16 at the cutting end of dual hypodermic needle 8 is the containment membrane 10 in an uninflated state (i.e. devoid of fluid or particulate matter).

During manufacture of the dual hypodermic needle 8, the neck of containment membrane 2 is disposed within channel 16, such that membrane 2 extends over and around the distal end of inner stylus 14. Thus, the interior of containment membrane 2 is retained in fluid communication with a central passage 18 extending through hollow stylus 14. More particularly, the distal end of inner stylus 14 extends into the interior of containment membrane 2 via the normally closed orifice 4 (of FIG. 1), which is now opened by the receipt therethrough of stylus 14. However, the elastic nature and spring-like memory of containment membrane 2 closes the orifice tightly around and prevents the inadvertent removal of membrane 2 from the distal end of stylus 14.

The presence of containment membrane 2 extending over the distal end of inner stylus 14 makes dual hypodermic needle 8 non-coring and thereby prevents the patient's tissue from entering the central passage 18 of stylus 14 during such time as when the outer trocar 10 is used to penetrate the urethral mucosa. Hence, trauma will be minimized since none of the patient's tissue will be removed with stylus 14 at the conclusion of the non-surgical process for implanting the prosthesis 1, which is now described while referring concurrently to FIGS. 2 and 3 of the drawings.

In operation, the physician initially exerts a downward force on dual hypodermic needle 8, so that the cutting end 12 of outer trocar 10 transurethrally or perineally penetrates the patient's urethral tissue and dialates an insertion channel to the bulbar urethra of the corpus spongiousum. The physician verifies the location of cutting end 12, so that containment membrane 2 may be properly positioned within the periurethral tissues.

Once a proper subcutaneous location has been achieved, the physician attaches a high pressure hypodermic syringe (not shown), or the like, to the proximal end of inner stylus 14. The hypodermic syringe contains the aforementioned fluid or suspended particulate matter 6, a regulated amount of which is percutaneously infused to the interior of containment membrane 2. Accordingly, a flow path is established between the hypodermic syringe and the containment membrane 2 by way of stylus 14, so that membrane 2 may be inflated, while in situ, with a controlled and measured supply of fluid or suspended particulate matter to thereby produce an increase in localized tissue volume and a correspondingly greater occlusive pressure necessary to achieve coaptive continence of the urethral mucosa.

Following the implantation and inflation of containment membrane 2, the physician exerts an upward pulling force on dual hypodermic needle 8 to remove the needle from the patient's tissue. The cavity produced during inflation of the containment membrane 2 within the patient's tissue produces a locating effect which removes the neck of the inflated membrane from its receipt by channel 16 at such time as when the hypodermic needle 8 is withdrawn from the patient's tissue. Accordingly, the normally closed orifice 4 (of FIG. 1) of containment membrane 2 automatically returns to the closed position whereby to prevent the migration of fluid or particles and avoid the possible deflation of membrane 2.

What is more, the channel 16 between outer trocar 10 and inner stylus 16, in which the neck of containment membrane 2 is received, may be interconnected with an external source of mechanical or hydraulic pressure 20. The application of sufficient pressure to the neck of containment membrane 2 by way of channel 16 will aid the physician in dispensing and positioning the membrane, after its inflation and just prior to the removal of hypodermic needle 8.

It may be noted that removal of the hypodermic needle 8 from the patient's urethral tissue will leave behind a relatively minor puncture wound. Thus, as another important advantage of this invention the patient will require a substantially shorter recovery time or no recovery time at all as compared to approximately two months or more if a prosthetic sphincter had been surgically implanted in a hospital. Moreover, the high cost, confinement and inconvenience commonly associated with such a hospital stay is minimized, since the present prosthesis 1 can be implanted by means of injection under a local anesthetic and the patient treated on a relatively cost efficient basis with a reduced hospital stay (e.g. about 24-48 hours).

Although the presently disclosed invention has been explained with reference to a single, implantable tissue expanding containment membrane 2, it is to be expressly understood that additional numbers of such containment membranes will usually be implanted, depending on the increased tissue volume and the resulting occlusive pressure which are required to permit the patient to be restored to continence. During and after one or more prostheses have been implanted, the physician will cystoscopically monitor the degree of the urethral mucosa. In the event that greater occlusive pressure is needed, the physician may implant a corresponding additional number of prostheses until patient continence is restored.

Thus, the present genitourinary prosthesis prevents the previous problem of small particle migration by virtue of the anti-migration containment membrane 2. Moreover, the prosthesis increases the pressure around the urethra in limited areas, thus reducing the risk of vascular ischemia and eventual urethral erosion, as are commonly caused by conventional surgically implanted genitourinary cuff sphincters.

It will be apparent that while a preferred embodiment of the invention has been shown and described, various modifications and changes may be made without departing from the true spirit and scope of the invention.

Having thus set forth a preferred embodiment, what is claimed is:

1. An injectable system for hypodermically implanting an inflatable containment membrane for increasing local tissue volume at the injection site, said system comprising:
   an inflatable containment membrane being in a normally uninflated condition;
   outer tube means having a cutting end for penetrating the tissue of a patient undergoing treatment, said uninflated containment membrane being located within said outer tube means;
   inner tube means extending through said outer tube means and communicating between the interior of said containment membrane and a source of material, said containment membrane being percutaneously infused with and inflated by material from said source via said inner tube means for simultaneously increasing local tissue volume while preventing the migration of the material contained within said membrane;
   said inner tube means and said outer tube means being concentrically aligned with and spaced from one another such that a first portion of said containment membrane is retained in the space between said inner and outer tube means and a second portion of said containment membrane is extended across the cutting end of said outer tube means to form a non-coring cutting end for preventing the patient's tissue from entering the outer tube means when the tissue is penetrated; and
   means for detaching said inflated membrane from the space between said inner and outer tube means so that said membrane remains implanted within the tissue of the patient.

2. The system recited in claim 1, wherein said containment membrane has an orifice biased toward a normally closed condition, said inner tube means extending through said orifice and holding said orifice open for percutaneously infusing and thereby inflating said containment membrane with material from said source.

3. An injectable system for hypodermically implanting an inflatable containment membrane for increasing local tissue volume at the injection site, said system comprising:
   an inflatable containment membrane being is a normally uninflated condition;
   outer tube means having a cutting end for penetrating the tissue of a patient undergoing treatment, said uninflated containment membrane being located within said outer tube means;
   inner tube means extending through said outer tube means and being concentrically aligned with and spaced from said inner tube means, a portion of the containment membrane being retained in the space between said inner and outer tube means, said inner tube means extending between the interior of said containment membrane and a source of material, said containment membrane being percutaneously infused with and inflated by material from said source via said inner tube means for simultaneously increasing local tissue volume while preventing the migration of the material contained within said membrane; and
   means connected to apply a force through the space between said inner and outer tube means for dispensing said containment membrane from said space after said membrane is inflated.

4. A hypodermic system for treating urinary incontinence by means of applying increased occlusive pressure to the urethra by producing a proportional increase of localized tissue volume proximal to the urethra, said system comprising:
   an inflatable containment membrane being in a normally uninflated condition and having an orifice biased in a normally closed condition;
   outer tube means having a cutting end for piercing a channel through the patient's urethral tissue, said uninflated containment membrane located within said outer tube means behind the cutting end thereof; and
   inner tube means located within said outer tube means and extending at a first end thereof through said orifice and into the interior of said containment membrane and communicating at the other end with a source of material, so that said membrane may be percutaneously infused with a supply of material from said source for inflating said membrane and thereby increasing both the local tissue volume proximal to the urethra and the occlusive pressure applied to the urethra, said outer tube means and said inner tube means being concentrically aligned with and spaced from one another to retain a portion of said containment membrane in the space therebetween, said containment membrane removably receiving said inner tube means through the orifice thereof for holding said orifice open, such that said containment membrane is detachably connected to said inner tube means and said containment membrane is inflated with material from said source.

5. The system recited in claim 4, further comprising means connected to apply a force through the space between said inner and outer tube means for detaching said containment membrane from said inner tube means and for dispensing said containment membrane from said space after said membrane is inflated.

6. A non-surgical method of implanting prosthesis comprising an inflatable containment membrane for treating urinary incontinence by increasing localized tissue volume and the occlusive pressure applied to a patient's urethra for holding the patient continent, said method comprising the steps of:

locating an inner filling tube within a hollow outer trocar tube having a cutting end, such that said inner filling tube and said outer trocar tube are arranged in coaxial alignment and spaced from one another;

locating a portion of an uninflated membrane within said outer trocar tube, such that said portion is retained in the space between said outer trocar tube and said inner filling tube and said inner filling tube communicates with the interior of said containment membrane for inflating said membrane;

piercing a small tunnel through the patient's urethral tissues with the cutting end of said outer trocar tube;

infusing said containment membrane with a supply of material from a source thereof by way of said inner filling tube to inflate said membrane;

detaching said inflated containment membrane from the space between said outer and inner tubes; and removing said outer trocar tube from the patient's urethral tissues.

7. The non-surgical method recited in claim 6, including the additional step of applying a force through the space between said outer trocar tube and said inner filling tube for detaching said inflated containment membrane therefrom.

* * * * *